(12) United States Patent
Coolidge et al.

(10) Patent No.: US 6,894,024 B2
(45) Date of Patent: May 17, 2005

(54) TREATMENT OF HIBERNATING MYOCARDIUM AND DIABETIC CARDIOMYOPATHY WITH A GLP-1 PEPTIDE

(75) Inventors: Thomas R. Coolidge, Falls Village, CT (US); Mario Ehlers, Lincoln, NE (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 94 days.

(21) Appl. No.: 09/982,978

(22) Filed: Oct. 22, 2001

(65) Prior Publication Data

US 2002/0146405 A1 Oct. 10, 2002

Related U.S. Application Data

(60) Provisional application No. 60/245,234, filed on Nov. 3, 2000, provisional application No. 60/242,139, filed on Oct. 23, 2000, and provisional application No. 60/241,834, filed on Oct. 20, 2000.

(51) Int. Cl.[7] .............................................. A61K 38/00
(52) U.S. Cl. ......................................................... 514/2
(58) Field of Search ............................................. 514/2

(56) References Cited

U.S. PATENT DOCUMENTS 6,235,481 B1 * 5/2001 Horikawa et al.
6,277,819 B1 * 8/2001 Efendic
6,399,601 B1 * 6/2002 Du Bois
6,441,015 B2 * 8/2002 Aspnes et al.

FOREIGN PATENT DOCUMENTS

WO 99/40788 8/1999
WO 00/34332 6/2000

OTHER PUBLICATIONS

International Search Report of International Application No. PCT/US01/32559, dated Mar. 18, 2003.
Cai and Kang, "Oxidative Stress and Diabetic Cardiomyopathy", *Cardiovascular Toxicology*, vol. 1, No. 3, pp. 181–193 (2001).

* cited by examiner

*Primary Examiner*—Michael Meller
(74) *Attorney, Agent, or Firm*—Arnold & Porter LLP

(57) ABSTRACT

Hibernating myocardium is characterized by viable myocardium with impaired function due to localized reduced perfusion. Hibernating myocytes retain cellular integrity, but cannot sustain high-energy requirements of contraction. High plasma levels of catecholamines, such as norepinepherine, are believed to be predictive of mortality from hibernating myocardium. Likewise, high levels of catecholamines lead to cardiomyopathy in patients with diabetes. GLP-1 reduces plasma norepinepherine levels, and it thus is useful in a method of treating hibernating myocardium or diabetic cardiomyopathy.

9 Claims, 4 Drawing Sheets

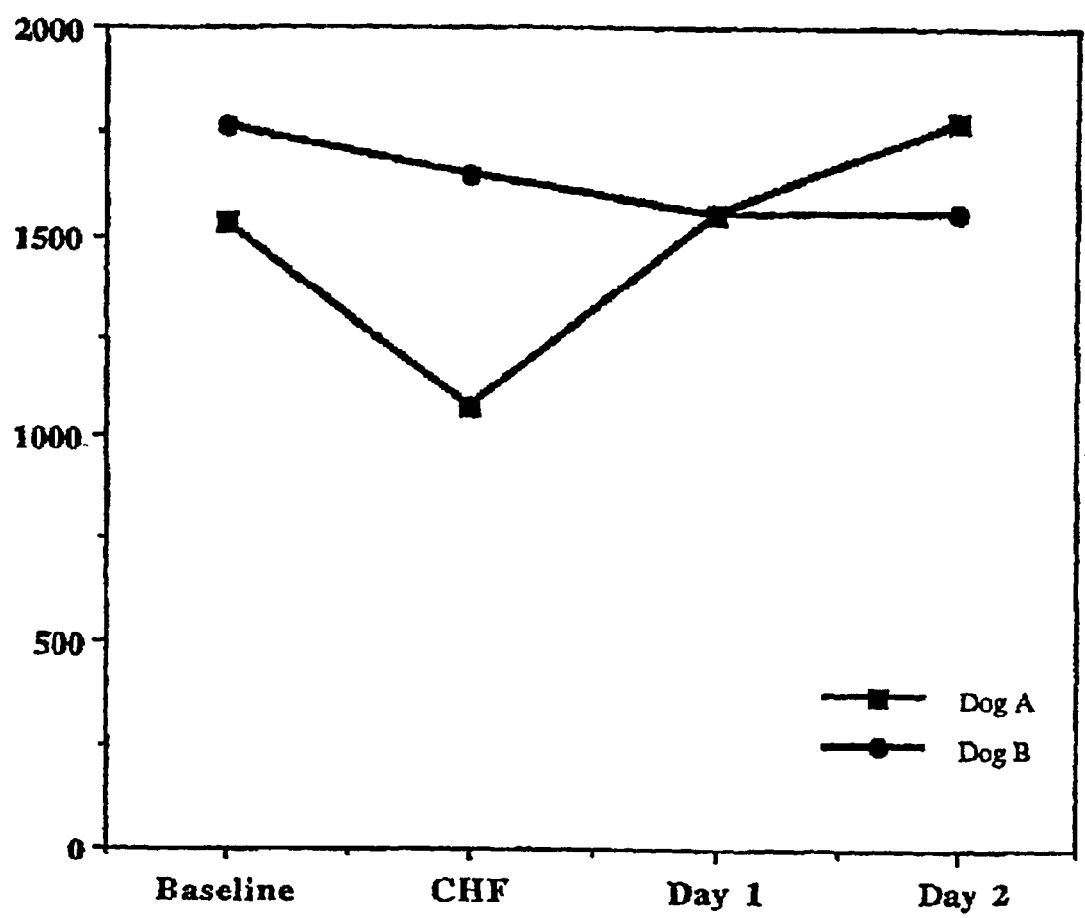

TREATMENT OF HIBERNATING MYOCARDIUM AND DIABETIC CARDIOMYOPATHY WITH A GLP-1 PEPTIDE

This application claims priority to U.S. application Ser. Nos. 60/241,834, filed Oct. 20, 2000, 60/242,139, filed Oct. 23, 2000, and 60/245,234, filed Nov. 3, 2000, all of which are hereby incorporated by reference.

BACKGROUND OF THE INVENTION

Heart failure continues to be a major health problem. Approximately four million persons in the U.S. population have heart failure. With a steadily aging population, four hundred thousand individuals experience new onset heart failure each year, with a five year mortality rate approaching fifty percent.

Rather than a single pathological entity, "heart failure" defines a clinical syndrome with many different etiologies that reflects a fundamental abnormality in effective mechanical performance of the heart, such that the heart is unable to meet the demands of the body. There are various forms of heart failure, including "forward" and "backward" heart failure. Backward failure, synonymous with congestive heart failure, is due to increase in venous pressure (i.e., increase in pressure in the veins that return blood to the heart) resulting from the inability of the heart to discharge its contents normally, leading to pulmonary and systemic congestion. By contrast, forward failure is caused by an inability of the heart to maintain normal tissue perfusion, resulting in fatigue, weakness, loss of weight, and impairment of cerebral function.

Hibernating Myocardium

"Hibernating myocardium" constitutes a significant fraction of forward heart failures, and it may or may not be accompanied by pulmonary or systemic congestion. This condition reflects localized depressed myocardial function as a result of chronic non-critical ischemia (hypoxia resulting from low blood supply). The degree of ischemia is not sufficient to produce necrosis (infarction), but it locally restricts myocardial oxygenation and fuel supply, such that a part of the myocardium becomes hypoactive or dormant. Hibernating myocytes remain viable but do not contribute to the pumping action of the heart. The severity of myocardial damage depends on the duration of hibernation. Eventually, the damage may become irreversible and may lead to heart failure when the extent of myocardial dysfunction is great enough to compromise cardiac performance and reduce the cardiac output; that is, ischemic cardiomyopathy may be the ultimate result of hibernating myocardium, if it is not treated appropriately.

Traditionally, hibernating myocardium has been treated by surgical revascularization through coronary bypass surgery or angioplasty. The inconvenience of surgery and the incidence of morbidity or restenosis associated with these techniques underscores the need for supplemental or alternative pharmacological intervention. Fath-Ordoubadi et al., Heart 82: 210–216 (1999) and Pagano et al., Curr. Opin. Cardiol. 14: 506–509 (1999). Effective pharmacological intervention would be especially useful where surgery is contraindicated, as in the case of mild hibernating myocardium, or where the patient's condition is considered too serious for surgery.

Congestive heart failure was first treated pharmacologically with vasodilators and inotropic agents, which increase cardiac muscle contractility. See WO 99/40788. While these drugs improved hemodynamics over the short term, recent studies have found a discrepancy between improved hemodynamics and clinical outcome. In fact, the only risk factor found predictive of morbidity associated with congestive heart failure is the plasma level of the catecholamine norepinepherine. Cohn et al., "Plasma norepinepherine as a guide to prognosis in patients with chronic congestive heart failure." N. Engl. J. Med. 311: 819–823 (1984); Lahiri et al., J. Cardio. Pharm. 33 (Suppl. 3): S9-S16 (1999). Thus, in the case of congestive heart failure, long term administration of inotropic agents is contraindicated. The compounds most useful to treat congestive heart failure have proven to be ACE inhibitors, which have a vasodilating effect, and multifunctional β-blockers like carvedilol, which exert an antiadrenergic effect. Lahiri et al. (1999).

Like congestive heart failure, there is evidence that administration of inotropic agents may worsen ischemia associated with hibernating myocardium. In one study, low level treatment with the inotrope dobutamine increased myocardial function in hibernating myocardium, but high levels of dobutamine increased myocardial demand to the point where it passed an ischemic threshold. Senioer et al., "Enhanced detection of myocardial ischaemia by stress dobutamine echocardiography utilising the 'biphasis' response of wall thickening during low and high dose dobutamine infusion." J. Am. Coll. Cardiol. 26: 26–32 (1995). This and similar studies have raised questions about the long term benefit to mortality from inotropic agents, despite their short term hemodynamic benefit. In particular, it has been proposed that further increases in myocardial demand may enhance ishemia associated with hibernating myocardium, thereby exacerbating necrosis and apoptosis. Lahiri et al. (1999).

Accordingly, it has been suggested that inotropic agents also are contraindicated for hibernating myocardium, and that hibernating myocardium should be treated with the same non-inotropic, or anti-adrenergic, agents that are used to treat congestive heart failure. By analogy to congestive heart failure, it has also been suggested that high plasma levels of catecholamines, like norepinepherine, are deleterious to clinical outcome of hibernating myocardium, because of their inotropic properties. Lahiri et al. (1999).

As there are only a handful of agents known to have limited efficacy for the long term treatment of hibernating myocardium, there remains a strong need for new therapeutic agents which have the potential to revitalize hibernating cells. In particular, there remains a strong need to find agents that can reduce the plasma blood level of catecholamines.

Diabetic Cardiomyopathy

Patients with diabetes are at high risk for developing diabetic cardiomyopathy (DCM). The exact etiology of this disease remains controversial, in part because many myocardial abnormalities are associated with diabetes. DCM is clearly defined, however, as a reversible cardiomyopathy that occurs in the absence of coronary atherosclerosis. Bell, Diabetes Care 18: 708–714 (1995). DCM is further characterized by myocardial fibrosis, that can be partially attributable to ischemia. Id. Hypertension, also characteristic of diabetes, can aggravate fibrosis to the point where DCM can become a serious, even fatal, condition. Id.

This hypertension is at least in part due to an abnormal activation of the sympathetic nervous system. Pallab et al., Am. J. Physiol. 252: E734–739. Among the manifestations of this aberrant activation is an increase in the level of norepinepherine in the heart, as well as its altered metabolism by the heart. Id. High levels of catecholamines, such as norepinepherine, in the heart or circulation result in the development of DCM. The accompanying myocardial damage is believed to be in part caused by the oxidative breakdown products of norepinepherine. Id. An ideal antihypertension agent for the diabetic patient thus would reduce the activation of the sympathetic nervous system without worsening hyperglycemia or hypoglycemia. Presently, very few compounds provide these characteristics.

SUMMARY OF THE INVENTION

Administration of GLP-1 has been found unexpectedly to suppress plasma blood levels of norepinepherine. By analogy to congestive heart failure, reduction in plasma norepinepherine levels will be expected to ease the ischemic stress to hibernating myocardium, thereby improving the clinical outcome. Accordingly, administration of GLP-1 will be useful in a method to treat hibernating myocardium, either alone or in conjunction with existing treatment regimes. Likewise, GLP-1 will be useful in reducing norepinepherine levels in the heart and/or plasma that are associated with the development of diabetic cardiomyopathy.

GLP-1 reduces plasma norepinepherine levels in a method of treating hibernating myocardium or diabetic cardiomyopathy. Thus, a method for treating hibernating myocardium or diabetic cardiomyopathy comprises administering a therapeutically effective amount of a GLP-1 molecule to said patient. A GLP-1 molecule also may be administered in therapeutically effective amount to a patient suffering from congestive heart failure or ischemic cardiomyopathy, particularly one who also has hibernating myocardium. A therapeutically effective amount of a GLP-1 molecule reduces the plasma and/or heart norepinepherine level. A GLP-1 molecule preferably is delivered intravenously or subcutaneously. The former is preferred for acute treatment with a GLP-1 molecule, while the latter is preferred in chronic treatment regimens.

Preferred GLP-1 molecules of the invention include GLP-1(7–36) amide, GLP-1(7–37), and exendin-4. GLP-1 molecules include those molecules that specifically bind to and activate the GLP-1 receptor.

BRIEF DESCRIPTION OF THE FIGURES

FIGS. 1–4 summarize the results obtained from two representative animals, Dog A (treatment) and Dog B (placebo).

FIG. 1 demonstrates changes in left ventricular (LV) contractility, as measured by the rate of change of LV pressure (dP/dt).

FIG. 2 demonstrates changes in LV ejection fraction (EF), as measured by percent emptying of the LV during systole.

FIG. 3 illustrates LV contraction, as reflected by the degree of wall thickening.

FIG. 4 reflects changes in overall cardiac function, as measured by cardiac output (CO), which is the volume of blood (in mL) pumped per minute.

DETAILED DESCRIPTION

Figure 1:
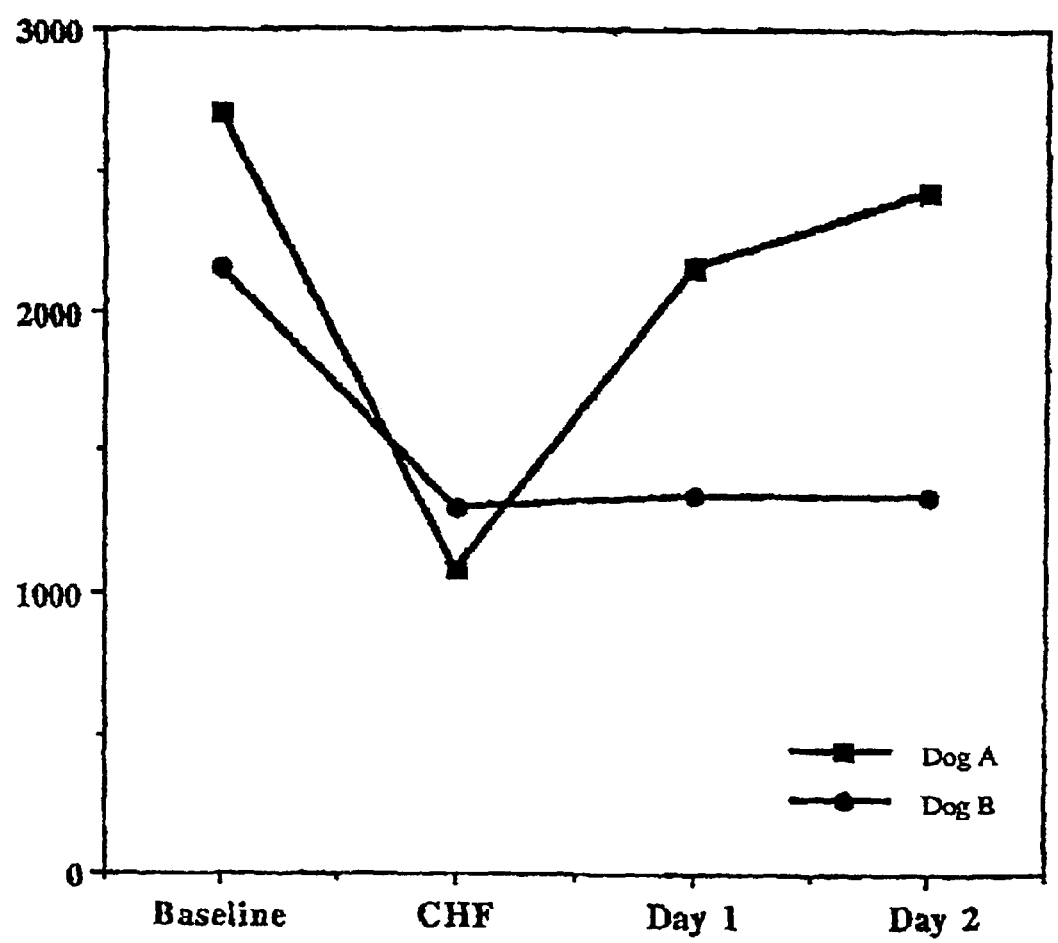

The present invention provides novel methods and compositions for treatment of hibernating myocardium (HM). In particular, the present invention includes a method of treating a patient with HM by administering a therapeutically effective amount of a GLP-1 molecule to the patient. The present inventors have surprisingly discovered that in mammals suffering from HM, administration of a GLP-1 molecule resulted in rapid recovery of heart function, compared with non-treated subjects. This recovery is associated with an unexpected decrease in the plasma levels of norepinepherine in treated mammals.

As used in this application "congestive heart failure" ("CHF") denotes a condition characterized by an increase in venous pressure that results from the inability of the heart to discharge its contents normally, leading to pulmonary and systemic congestion. The heart muscle of a patient with CHF has a reduced ability to act as a pump. CHF is accompanied by circulatory and neurohumoral changes which result in failure to deliver sufficient blood and oxygen supply to peripheral tissues and vital organs.

"Hibernating myocardium" means viable myocardium with impaired function due to reduced perfusion. HM retains cellular integrity, but cannot sustain high-energy requirements of contraction. HM is distinguished from infarcted myocardium, which is irreversible myocardial damage with formation of a scar, and from stunned myocardium, which is myocardium with contractile dysfunction despite normalization of perfusion. Jadvar et al., *RadioGraphics* 19: 915–926 (1999).

Clinically, HM may be detected by the use of dobutamine stress echocardiography. Shan et al., In Cardiology Clinics, G. Aurigemma, ed., W. B. Saunders Co., Philadelphia, Vol. 17, No. 3, pages 539–553 (1999). HM may also be detected by cardiac positron emission tomography (PET), which is more accurate than single photon emission tomography (SPECT). PET with 2-(fluorine-18) fluoro-2-deoxy-D-glucose is considered the standard of reference for determining regional or left ventricular function, following revascularization, to identify viable hibernating myocardium. Stress magnetic resonance imaging has been used to further diagnose hibernating myocardium and distinguish this disease from other myocardial disease states. HM is characterized by decrease in left ventricular (LV) function that is moderate, compared to the severe decrease associated with irreversible dysfunction or scarring. The degree of systolic wall thickening (SWT) is also characteristic of myocardial hibernation. SWT is severely decreased at rest, compared to normal or irreversibly damaged or scarred myocardium, and SWT dysfunction distinctively improves during stress. Sensky et al., *Radiology* 215: 608–614.

"Diabetic cardiomyopathy" (DCM) is defined as a reversible cardiomyopathy in diabetics that occurs in the absence of coronary atherosclerosis. Bell, *Diabetes Care* 18: 708–714 (1995); Fein, *Diabetes Care* 13: 1169–1179 (1990). DCM is characterized by myocardial hypertrophy and fibrosis. Microvascular pathology is also present, and, in some cases, both congestive and restrictive cardiomyopathies are present. Id.

The "paced dog" model, used in the Example below, provides a system to study HM, because the exertion of the heart exceeds the heart's ability to respond, which creates an energy-limited situation. Other suitable animal models are available to study chronically dysfunctional viable myocardium, in dogs and pigs, for example, which allow laboratory study of therapeutic regimens. For example, the fixed LAD (left anterior descending artery) stenosis model in pigs demonstrates cardiac dysfunction with reduced myocardial perfusion that is analogous to humans with HM in the absence of infarction. Canty et al., *Am. J. Physiol.* 277: H417–H422 (1999). Similar animal models in diabetic dogs, mice and rats are available for the study of DCM. Bell (1995); Fein (1990).

A "GLP-1 molecule" includes the following. Mammalian GLP peptides and glucagon are encoded by the same gene.

In the ileum, the phenotype is processed into two major classes of GLP peptide hormones, namely GLP-1 and GLP-2. GLP-1 (1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated by post-translational processing to yield GLP-1 (1–36) $NH_2$ which has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:2); or is enzymatically processed to yield GLP-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1 (7–37) can also be amidated to yield GLP-1 (7–36) amide which is the natural form of the GLP-1 molecule, and which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:4) and in the natural form of the GLP-1 molecule. Likewise, GLP-1(1–36) ($NH_2$) can be processed to GLP-1 (7–36) ($NH_2$).

Intestinal L cells secrete GLP-1 (7–37) (SEQ ID NO:3) and GLP-1(7–36)$NH_2$ (SEQ ID NO: 4) in a ratio of 1 to 5, respectively. These truncated forms of GLP-1 have short in situ half-lives, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5); and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6); respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5) and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6), have been speculated to affect hepatic glucose production, but do not stimulate production or release of insulin from the pancreas.

As used in this specification, the term "GLP-1 molecule" includes GLP-1 (1–37), GLP-1 (1–36) $NH_2$, GLP-1 (7–37), GLP-1 (7–36) $NH_2$ ("GLP-1 (7–36) amide") (collectively referred to as "GLP-1 peptides"). The present invention includes the use of recombinant human GLP-1 peptides as well as GLP-1 peptides derived from other species, whether recombinant or synthetic.

"GLP-1 molecule" further denotes biologically active variants, analogs and derivatives of GLP-1 peptides. "Biologically active," in this context, means having GLP-1 (7–36) biological activity, but it is understood that the activity of the variant can be either less potent or more potent than native GLP-1 (7–36) amide. GLP-1 (7–36) amide is a native, biologically active form of GLP-1. See Göke et al., Diabetic Medicine. 13:854–860 (1996). GLP-1 molecules of the present invention include polynucleotides that express agonists of GLP-1, i.e. activators of the GLP-1 receptor molecule and its secondary messenger activity found on insulin-producing β-cells, among others. GLP-1 mimetics that also are agonists of GLP-1 receptors on β-cells include, for example, chemical compounds specifically designed to activate the GLP-1 receptor.

GLP-1 molecule biological activity can be determined by in vitro and in vivo animal models and human studies as is well known to the skilled artisan. Included as GLP-1 molecules are any molecules, whether they be peptides, peptide mimetics, or other molecules that bind to or activate a GLP-1 receptor, such as the GLP-1 (7–36) amide receptor, and its second messenger cascade. GLP-1 receptors are cell-surface proteins found, for example, on insulin-producing pancreatic β-cells. The GLP-1 (7–36) receptor has been characterised in the art. Methods of determining whether a chemical or peptide binds to or activates a GLP-1 receptor are known to the skilled artisan and are preferably carried out with the aid of combinatorial chemical libraries and high throughput screening techniques. GLP-1 molecules include species having insulinotropic activity and that are agonists of the GLP-1 receptor molecule and its second messenger activity on insulin producing β-cells, among others.

GLP-1 biological activity can be determined by standard methods, in general, by receptor-binding activity screening procedures which involve providing appropriate cells that express the GLP-1 receptor on their surface, for example, insulinoma cell lines such as RINmSF cells or INS-1 cells. See Mosjov, Int. J. Peptide Protein Res. 40: 333–343 (1992) and EP 708170. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds activate the receptor and generate a signal.

Polyclonal and monoclonal antibodies can be utilized to detect purify and identify GLP-1 like peptides for use in the methods described herein. Antibodies such as ABGA1178 detect intact unspliced GLP-1 (1–37) or N-terminally-truncated GLP-1 (7–37) or (7–36) amide. Other antibodies detect on the very end of the C-terminus of the precursor molecule, a procedure which allows by subtraction to calculate the amount of biologically active truncated peptide, such as GLP-1 (7–37) amide. See Orskov et al., Diabetes 42: 658–661 (1993) and Orskov et al., J. Clin. Invest. 87: 415–423 (1991).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

Agonists of glucagon-like peptide that exhibit activity through the GLP-1 (7–36) amide receptor have been described in EP 0708179; Hjorth et al., J. Biol. Chem. 269 (48): 30121–30124 (1994); Siegel et al., Amer. Diabetes Assoc. 57th Scientific Sessions, Boston (1997); Hareter et al., Amer. Diabetes Assoc. 57th Scientific Sessions, Boston (1997); Adelhorst et al., J. Biol. Chem. 269(9): 6275–6278 (1994); Deacon et al., 16th International Diabetes Federation Congress Abstracts, Diabetologia Supplement (1997); Irwin et al., Proc. Natl. Acad. Sci. USA. 94: 7915–7920 (1997); Mosjov, Int. J. Peptide Protein Res. 40: 333–343 (1992). See also Göke et al., Diabetic Medicine 13: 854–860 (1996). Recent publications disclose Black Widow GLP-1 and $Ser^2$ GLP-1. See Holz et al., Comparative Biochemistry and Physiology, Part B 121: 177–184 (1998) and Ritzel et al., "A synthetic glucagon-like peptide-1 analog with improved plasma stability," J. Endocrinol. 159(1): 93–102 (1998).

"GLP-1 molecules" also include peptides that are encoded by polynucleotides that express biologically active GLP-1 variants as defined herein. Also included in the present invention are GLP-1 molecules that are peptides containing one or more amino acid substitutions, additions or deletions, compared with GLP-1 (7–36) amide. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue. Examples of conservative substitution include the substitution of one hydrophobic residue, such as isoleucine, valine, leucine or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

| ORIGINAL RESIDUE | EXEMPLARY SUBSTITUTIONS |
|---|---|
| ALA | SER, THR |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that GLP-1 peptide variants include the above described peptides which have been chemically derivatized or altered, for example, peptides with non-natural amino acid residues (e.g., taurine residue, beta and gamma amino acid residues and D-amino acid residues), C-terminal functional group modifications such as amides, esters, and C-terminal ketone modifications and N-terminal functional group modifications such as acylated amines, Schiff bases, or cyclization, such as found for example in the amino acid pyroglutamic acid.

Also included in the present invention are peptide sequences having greater than 50 percent sequence identity, and preferably greater than 90 percent sequence identity to (1) SEQ ID NOS:1, 2, 3, 4; and (2) to truncated sequences thereof. As used herein, sequence identity refers to a comparison made between two molecules using standard algorithms well known in the art. The preferred algorithm for calculating sequence identity for the present invention is the Smith-Waterman algorithm, where SEQ ID NO:1 is used as the reference sequence to define the percentage identity of polynucleotide homologs over its length. The choice of parameter values for matches, mismatches, and inserts or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and $-\frac{1}{3}$ for a mismatched residue (a residue being either a single nucleotide or single amino acid) (Waterman, Bulletin of Mathematical Biology 46:473–500 (1984)). Insertions and deletions (indels), x, are weighted as $$x_k = 1 + k/3,$$

where k is the number of residues in a given insert or deletion (Id.).

For instance, a sequence that is identical to the 42 amino acid residue sequence of SEQ ID NO:1, except for 18 amino acid substitutions and an insertion of 3 amino acids, would have a percent identity given by:

[(1×42 matches)−(⅓×18 mismatches) −(1+3/3 indels)]/42=81% identity.

Also included in "GLP-1 molecules" of the present invention are six peptides in Gila monster venoms that are homologous to GLP-1. Their sequences are compared to the sequence of GLP-1 in Table 1.

TABLE 1

```
Position 1
a.  H A E G T F T S D V S S Y L E G Q A A K E F I A W L V K G R (NH2)

b.  H S D G T F T S D L S K Q M E E E A V R L F I E W L K N G G P S S G A P P P S (NH2)

c.              D L S K Q M E E E A V R L F I E W L K N G G P S S G A P P P S (NH2)

d.  H G E G T F T S D L S K Q M E E E A V R L F I E W L K N G G P S S G A P P P S (NH2)

e.  H S D A T F T A E Y S K L L A K L A L Q K Y L E S I L G S S T S P R P P S S f.  H S D A T F T A E Y S K L L A K L A L Q K Y L E S I L G S S T S P R P P S g.  H S D A I F T E E Y S K L L A K L A L Q K Y L A S I L G S R T S P P P (NH2)

h.  H S D A I F T Q Q Y S K L L A K L A L Q K Y L A S I L G S R T S P P P (NH2)

a = GLP-1 (7–36) amide (SEQ. ID NO:4)

b = Exendin 3 (SEQ. ID NO:7).
```

TABLE 1-continued

```
c = Exendin 4 (9-39 (NH2(SEQ. ID NO:8).

d = Exendin 4 (SEQ. ID NO:9).

e = Helospectin I (SEQ. ID NO:10).

f = Helospectin II (SEQ. ID NO:11).

g = Helodermin (SEQ. ID NO:12).

h = Q8, Q9 Helodermin (SEQ. ID No:13).
```

Peptides (a, b, d, e, f and g) are homologous in positions 1, 7, 11 and 18. GLP-1 and exendins are further homologous in positions, 4, 5, 6, 8, 9, 15, 22, 23, 25, 26 and 29. In position 2, A, S and G are structurally similar. In position 3, residues D arid E (Asp and Glu) are structurally similar. In positions 22 and 23, F (Phe) and I (Ile) are structurally similar to Y (Tyr) and L (Leu), respectively. Likewise, in position 26, L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 molecules of the invention that are peptides that can be made by solid state chemical peptide synthesis. Such peptides can also be made by conventional recombinant techniques using standard procedures described in, for example, Sambrook et al., "Molecular Cloning, a Laboratory Manual," Cold Spring Harbor Press, N.Y (1989). "Recombinant", as used herein, means that a gene is derived from a recombinant (e.g., microbial or mammalian) expression system which has been genetically modified to contain polynucleotide encoding a GLP-1 molecule as described herein.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can be employed for final purification steps.

The GLP-1 molecule peptides of the present invention may be a naturally purified product, or a product of chemical synthetic procedures, or produced by recombinant techniques from prokaryotic or eukaryotic hosts (for example, by bacteria, yeast, higher plant, insect and mammalian cells in culture or in vivo). Depending on the host employed in a recombinant production procedure, the polypeptides of the present invention are generally non-glycosylated, but may be glycosylated. Particularly preferred GLP-1 molecules of the invention are GLP-1(7–36) amide, and GLP-1(7–37) and exendin-4.

Therapeutic Methods

The therapeutic methods of the invention are useful for treating any patient suffering from HM. Such a patient also may suffer from congestive heart failure. Alternately, such a patient may suffer from, or be predisposed to, DCM. Typically, a GLP-1 molecule of the invention will be administered in a parenteral formulation. Other well known methods for administering a GLP-1 molecule to a patient suffering from HM also can be employed in the methods of the invention. These administration methods include, but are not limited to, subcutaneous or micropressure injection, external or implant pump, depot injection, and other types of prolonged application dispensing devices. Other methods of administration, such as transdermal or transmembrane administration, using patch or buccal means, also can be employed. Oral administration also may be suitable. Pulmonary administration, such as inhalation, also can be employed.

The route of administration may be optimized for particular treatments regimens. If chronic treatment of HM is required, for example, administration preferably will be via continuous subcutaneous infusion, using an external infusion pump. By contrast, if acute treatment of HM is required, as in the case of associated heart failure, then intravenous infusion is preferred.

The timing of administration of a GLP-1 molecule will depend on the nature of the condition being treated. Administration of a GLP-1 molecule may be as soon as HM or DCM is diagnosed, and the administration can be either continuous or on an intermittent basis, for as long as necessary. For acute conditions, where heart failure suddenly worsens, several hours to several days of continuous infusion are preferred. For chronic treatment, a GLP-1 molecule may be administered for weeks to months, even years, by continuous infusion.

The amount of a GLP-1 molecule that should be administered will vary according to the severity of the conditions and the patient. An advantage of using GLP-1 (7–36) amide is that high doses can be used without consequent hypoglycemia, because the action of GLP-1 (7–36) amide is dependent on glucose levels. Therefore, doses of up to 10.0 nmol/kg can be used without adverse effects. For intravenous administration, a typical dose of a GLP-1 molecule will be 1.5 pmol/kg/min. The range of the dose may vary between about 0.1–10 pmol/kg/min. For subcutaneous administration, the optimal dose is 5 pmol/kg/min, with a range between about 0.5–50 pmol/kg/min.

GLP-1 can also be co-administered with other therapeutic agents that are known for treating HM or DCM. For HM, these therapeutic agents include carvedilol, ACE inhibitors, and other anti-HM drugs, such as nitrates and hydralazine, bisoprolol, and metoprolol. See Lahiri et al. GLP-1 can be administered as an adjunct to surgerical treatment of HM, by cardiac by-pass surgery or by angioplasty, for example. Administration of GLP-1 may be made to an individual before, during or following surgical treatment. Where surgery is not indicated or is undesirable, GLP-1 may be administered as an alternative treatment regime. Treatment with GLP-1 would be especially useful, not only when surgery is contraindicated, as in the case of mild hibernating myocardium, but also when the patient's condition is considered too serious for surgery. ACE inhibitors likewise are among the preferred compounds for treating DCM. Bell (1995).

"Treating" embraces the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. A method to treat diabetic cardiomyopathy thus may comprise a method to reduce plasma norepinepherine levels in a diabetic patient, since the latter may lead to or aggravate cardiomyopathy.

EXAMPLE 1

Beagle dogs were fitted with telemetry devices that permit long-term ambulatory data collection in conscious animals. These devices measured LV pressure, myocardial oxygen consumption ($MVO_2$, an expression of myocardial efficiency), coronary flow (CBF), and cardiac output (CO). The dogs were "paced," such that heart rate was forced up to about 240 beats per minute, for 3–4 weeks, which induces moderate HM in a predictable manner. This HM dog model is an accepted model for assessing the effectiveness of treatments for HM. Kiuchi et al., "Myocardial beta-adrenergic receptor function during the development of pacing-induced heart failure." *J. Clin. Invest.* 91: 907–914 (1993).

Following induction of HF, five dogs were given an intravenous infusion of rGLP-1 (7–36) amide (1.5 pmol/kg/min) for 48 hours and four dogs served as controls. During the treatment period, "pacing" was discontinued. Plasma catecholamines were assessed before and after infusion, along with LV pressures, coronary and systemic hemodynamics, and $MVO_2$. The results are summarized in Table 1. GLP-1 treatment significantly reduced ($*p<0.05$) plasma norepinepherine (NE) levels from $2.30\pm0.15$ nmol/ml to $1.62\pm0.11$ nmol/ml. Moreover, GLP-1 treatment significantly ($*p<0.05$) increased left ventricular pressure (LVP), left ventricular contractility (LV dP/dt), cardiac output (CO), coronary blood flow (CBF), and myocardial oxygen consumption ($MVO_2$), while significantly decreasing LV end-diastolic pressure (LVEDP). These data indicate that the rGLP-1-treated dogs demonstrated a remarkable recovery of heart function within 48 hours of GLP-1 treatment. This was associated with increases in oxidative phosphorylation as measured by $MVO_2$, suggesting improved myocardial energetics. Thus, GLP-1 infusion is associated with decreased plasma NE and significant improvement in myocardial energetics. The placebo-treated control dogs did not, in this study, show the same degree of heart failure as the GLP-1 group before treatment. However, the control animals clearly had compromised hemodynamics, which did not improve during the 48-hour placebo treatment period.

FIGS. 1–4 summarize the results obtained from two representative animals, Dog A (treatment) and Dog B (placebo). FIG. 1 reflects changes in left ventricular (LV) contractility, as measured by the rate of change of LV pressure (dP/dt). In the treated animal (dog A), pacing reduced contractility by 60%, as expected in a model of HM. Remarkably, 24 hours of GLP-1 treatment restored contractility to 80% of baseline, and 48 hours of treatment restored contractility to 90% of baseline. In contrast, in the control animal (dog B), pacing reduced contractility by 40%, which did not improve with placebo infusion over the next 48 hours. Hence, GLP-1 markedly improves myocardial contractility after pacing-induced heart failure (or hibernating myocardium).

Figure 2:
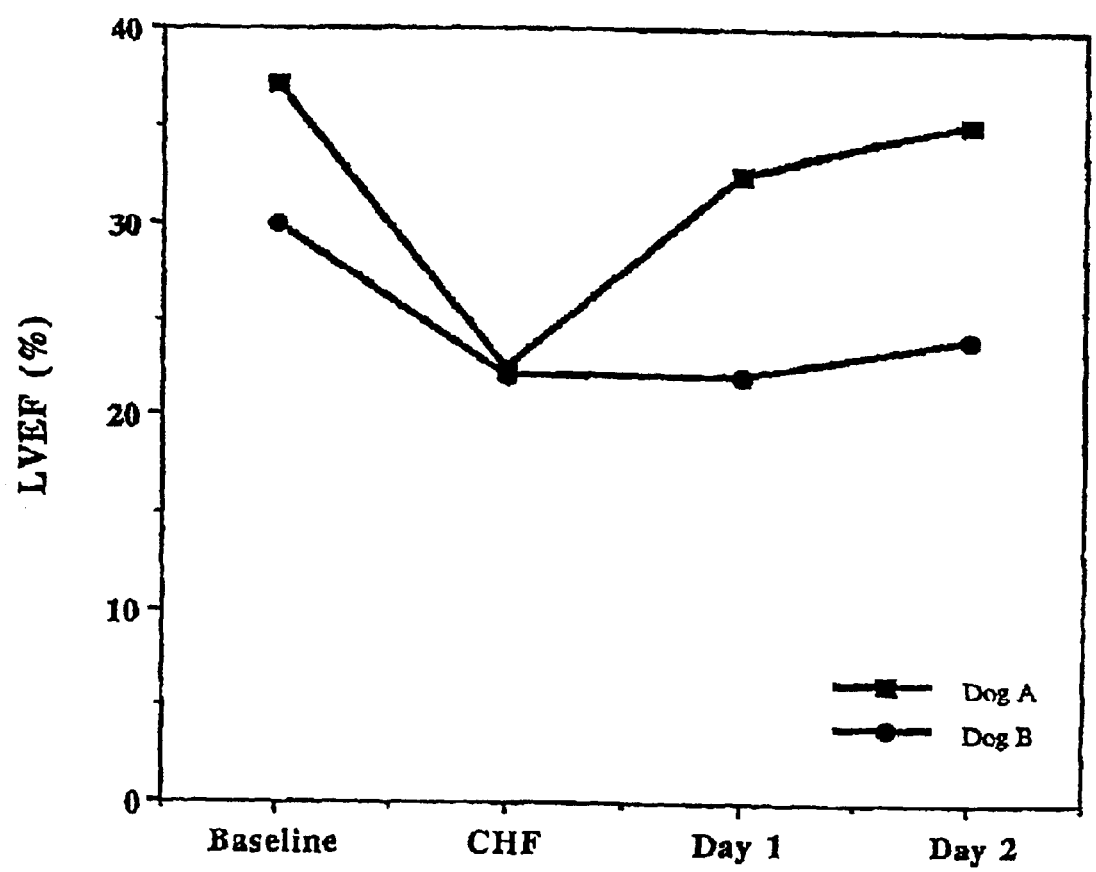

FIG. 2 reflects changes in LV ejection fraction (EF), as measured by percent emptying of the LV during systole. In the treated animal (dog A), pacing reduced LVEF by 40%, which then improved to 88% and 95% of the baseline value after 24 and 48 hours of GLP-1 treatment, respectively. In the control animal (dog B), pacing reduced LVEF by about 30%, which subsequently improved only modestly over the next 48 hours. Hence, GLP-1 treatment improves LVEF after pacing-induced heart failure.

Figure 3:
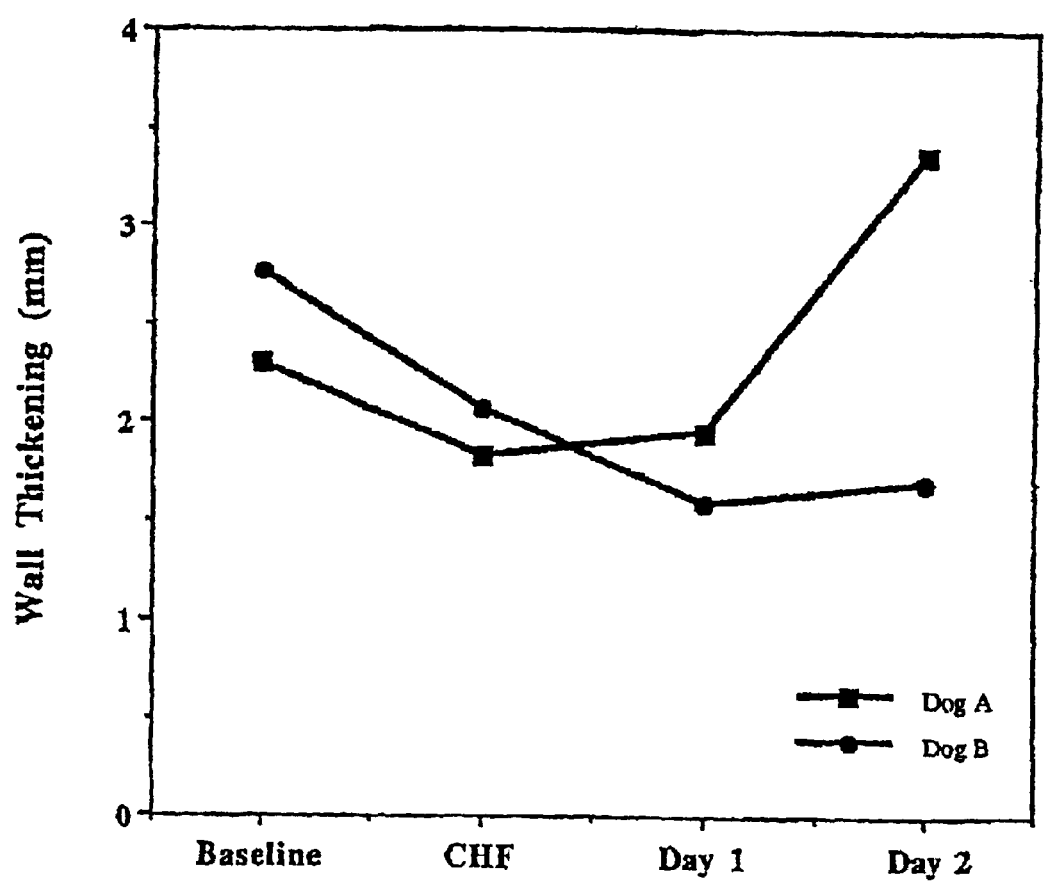

FIG. 3 illustrates LV contraction, as reflected by the degree of wall thickening. In the treated animal (dog A), pacing resulted in a 20% reduction of wall thickening, which recovered after 24 hours of GLP-1 treatment and actually increased to 147% of the baseline value after 48 hours of treatment. In contrast, in the control animal (dog B), wall thickening was reduced by 25% after pacing, and this declined further to 62% of the baseline value over the 48-hour placebo treatment period. Hence, GLP-1 treatment markedly improves LV contraction after pacing-induced heart failure.

FIG. 4 reflects changes in overall cardiac function, as measured by cardiac output (CO), which is the volume of blood (in mL) pumped per minute. CO is a product of stroke volume (volume of blood in mL expelled per systolic contraction) and heart rate (beats per minute). CO is a reflection of myocardial contractility (i.e., the intrinsic force of contraction) as well as of systemic hemodynamics, including pre-load (i.e., venous filling pressures) and after-load (i.e., mean arterial pressure and systemic vascular resistance). In the treated animal (dog A), pacing resulted in a 30% reduction of CO, which was restored to baseline levels after 24 hours of GLP-1 treatment, and actually increased to 116% of baseline after 48 hours of treatment. In contrast, in the control animal (dog B), CO only fell by 7% after pacing, which may indicate that in this particular animal there was hemodynamic compensation for the reduced myocardial contractility (FIG. 1) and LVEF (FIG. 2), thereby maintaining CO near normal. Nevertheless, over the 48-hour placebo treatment, CO declined further, to 89% of baseline. Hence, GLP-1 treatment markedly improves cardiac output after pacing-induced heart failure.

TABLE 2

|  | GLP-1 | | CONTROL | |
| --- | --- | --- | --- | --- |
|  | BEFORE | AFTER | BEFORE | AFTER |
| NE (nmol/ml) | 2.30 ± 0.15 | 1.62 ± 0.11* | 1.55 ± 0.37 | 1.87 ± 0.14* |
| LVP (mm Hg) | 98 ± 2 | 108 ± 2* | 109 ± 4 | 104 ± 2 |
| LVEDP (mm Hg) | 25 ± 1 | 15 ± 1* | 25 ± 2 | 21 ± 2 |
| dP/dt (mm Hg/s) | 1127 ± 86 | 2212 ± 86* | 1650 ± 100 | 1736 ± 112 |
| CO (ml/min) | 1.38 ± 0.15 | 1.82 ± 0.12* | 1.60 ± 0.10 | 1.42 ± 0.14 |
| CBF (ml/min) | 27 ± 1 | 37 ± 3* | 33 ± 3 | 33 ± 1 |
| $MVO_2$ (ml $O_2$/min) | 246 ± 18 | 297 ± 16* | 280 ± 38 | 287 ± 23 |

What is claimed is:

1. A method of treating a patient suffering from diabetic cardiomyopathy, comprising administering an effective amount of compound selected from the group consisting of Glucagon-Like Peptide-1 (GLP-1), GLP-1 analogs, and GLP-1-like peptides, to a patient suffering from diabetic cardiomyopathy.

2. The method of claim 1, wherein the administration is continuous.

3. The method of claim 1, wherein the administration is parenteral.

4. The method of claim 1, wherein said effective amount of said compound is effective to cause a reduction in the plasma or heart norepinepherine level.

5. The method of claim 3, wherein said compound is administered in a dose of from about 0.1–10 pmol/kg/min.

6. The method of claim 1 wherein said compound is administered subcutaneously in a dose of about 0.5–50 pmol/kg/min.

7. The method of claim 1 wherein said compound is administered in a dose of up to 10.0 nmol/kg.

8. The method of claim 1, wherein said compound is administered intravenously in a dose of about 0.1–10 pmol/kg/min.

9. The method of claim 1, wherein said compound is selected from the group consisting of GLP-1(1–37), GLP-1(1–36)$NH_2$, GLP-1(7–37), and GLP-1(7–36)NH2.

* * * * *

SEQUENCE LISTING

<160> NUMBER OF SEQ ID NOS: 13

<210> SEQ ID NO 1
<211> LENGTH: 37
<212> TYPE: PRT
<213> ORGANISM: Unknown Organism
<220> FEATURE:
<223> OTHER INFORMATION: Description of Unknown Organism: Mammalian GLP peptide

<400> SEQUENCE: 1

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: Unknown Organism
<220> FEATURE:
<223> OTHER INFORMATION: Description of Unknown Organism: Mammalian GLP peptide

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: Unknown Organism
<220> FEATURE:
<223> OTHER INFORMATION: Description of Unknown Organism: Mammalian GLP peptide

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Unknown Organism
<220> FEATURE:
<223> OTHER INFORMATION: Description of Unknown Organism: Mammalian GLP peptide

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

```
<210> SEQ ID NO 5
<211> LENGTH: 29
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 5

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: Unknown Organism
<220> FEATURE:
<223> OTHER INFORMATION: Description of Unknown Organism: Truncated form
      of GLP-1

<400> SEQUENCE: 6

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Unknown Organism
<220> FEATURE:
<223> OTHER INFORMATION: Description of Unknown Organism: Exendrin 3

<400> SEQUENCE: 7

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 8
<211> LENGTH: 31
<212> TYPE: PRT
<213> ORGANISM: Unknown Organism
<220> FEATURE:
<223> OTHER INFORMATION: Description of Unknown Organism: Exendrin 4
      (9-39(NH2)

<400> SEQUENCE: 8

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
                20                  25                  30

<210> SEQ ID NO 9
<211> LENGTH: 39
<212> TYPE: PRT
<213> ORGANISM: Unknown Organism
<220> FEATURE:
<223> OTHER INFORMATION: Description of Unknown Organism: Exendrin 4

<400> SEQUENCE: 9
```

-continued

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Unknown Organism
<220> FEATURE:
<223> OTHER INFORMATION: Description of Unknown Organism: Helospectin I

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 11
<211> LENGTH: 37
<212> TYPE: PRT
<213> ORGANISM: Unknown Organism
<220> FEATURE:
<223> OTHER INFORMATION: Description of Unknown Organism: Helospectin II

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Unknown Organism
<220> FEATURE:
<223> OTHER INFORMATION: Description of Unknown Organism: Helodermin

<400> SEQUENCE: 12

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Unknown Organism
<220> FEATURE:
<223> OTHER INFORMATION: Description of Unknown Organism:
    Q8, Q9 heliodermin

<400> SEQUENCE: 13

His Ser Asp Ala Ile Phe Thr Gln Gln Tyr Ser Lys Leu Leu Ala Lys
1               5                   10                  15

-continued

```
Leu Ala Leu Gln Lys Tyr Leu Ala Ser Ile Leu Gly Ser Arg Thr Ser
            20                  25                  30
Pro Pro Pro
        35
```